United States Patent
Chang et al.

(10) Patent No.: US 7,270,961 B2
(45) Date of Patent: Sep. 18, 2007

(54) IN VITRO ASSAY FOR QUANTITATING SECRETED ANTIBODIES IN LYMPHOCYTE SUPERNATANT FOR EVALUATION OF VACCINE OR ANTIGEN INDUCED SPECIFIC ANTIBODY SECRETION FROM EX VIVO CIRCULATING ANTIBODY-SECRETING LYMPHOCYTES

(75) Inventors: Hui Sunny Chang, 10326 Champions Way, Laurel, MD (US) 20723; David Sack, Dhaka (BD)

(73) Assignee: Hui Sunny Chang, Laurel, MD (US)

( * ) Notice: Subject to any disclaimer, the term of this patent is extended or adjusted under 35 U.S.C. 154(b) by 454 days.

(21) Appl. No.: 10/412,011

(22) Filed: Apr. 11, 2003

(65) Prior Publication Data

US 2004/0082019 A1 Apr. 29, 2004

Related U.S. Application Data

(60) Provisional application No. 60/372,437, filed on Apr. 16, 2002.

(51) Int. Cl.
*G01N 33/53* (2006.01)
(52) U.S. Cl. .................. 435/7.1; 530/380; 530/386; 530/387.1; 530/412; 530/413; 530/866; 530/861; 530/862; 530/863; 435/2; 435/340; 435/326; 435/327; 435/377; 435/383

(58) Field of Classification Search ............... 530/380, 530/386, 387.1, 412, 413, 866, 861–863; 435/2, 340, 326–327, 377, 383
See application file for complete search history.

(56) References Cited

U.S. PATENT DOCUMENTS 5,653,986 A * 8/1997 Morris et al. ............ 424/261.1

OTHER PUBLICATIONS

Lane et al., Journal of Experimental Medicine. vol. 154, Oct. 1981, pp. 1043-1057.*
Peters et al., The Journal of Immunology. vol. 130, No. 2, Feb. 1983, pp. 678-680.*
Rebelatto et al., Veterinary Immunology and Immunopathology. vol. 83. 2001. pp. 93-105.*
Volkman et al., Proc. Natl. Acad. Sci. vol. 78, No. 4, pp. 2528-2531, Apr. 1981.*

* cited by examiner

*Primary Examiner*—Bao-Thuy L. Nguyen

(57) ABSTRACT

The present invention provides methods of quantitating recent secreted antigen specific antibodies from supernatant of antibody secreting cells (ASC) in vitro culture for evaluation of vaccine or antigen induced antigen specific antibody secretion without ex vivo antigen stimulation.

14 Claims, No Drawings

IN VITRO ASSAY FOR QUANTITATING SECRETED ANTIBODIES IN LYMPHOCYTE SUPERNATANT FOR EVALUATION OF VACCINE OR ANTIGEN INDUCED SPECIFIC ANTIBODY SECRETION FROM EX VIVO CIRCULATING ANTIBODY-SECRETING LYMPHOCYTES

The application claim priority of provisional application Ser. No. 60/372,437 of file on Apr. 16, 2002.

BACKGROUND OF THE INVENTION

1. Field of the Invention

The present invention is direct to the field of vaccinology, and epidemiology. Specifically, the present invention provides method for quantitating recent secreted antigen specific antibodies from lymphocyte supernatant for evaluation of vaccine or antigen induced specific antibody secretion from ex vivo circulating lymphocytes without ex vivo antigen stimulation.

2. Related Art

This technology is a novel method for measuring in vitro antibody secretion from tissue culture of B lymphocytes in the peripheral blood mononucleus cells (PBMC). Instead of enumerating antibody-secreting cells in the ELISPOT assay, this technology quantifies recent antigen specific secreted antibodies from a fixed concentration of PBMC cells rather than accumulative soluble antibodies in the serum after immunization with a vaccine or exposure to antigen(s). The soluble antibodies in the serum is removed in this method.

3. General Purpose

A clinical trial using this technology demonstrated that the post-immunization human PBMC cells secreted antibodies to cholera toxin in the cell supernatants without any in vitro antigen stimulation after an oral vaccination with a killed cholera vaccine which is an antigenic substance, an antigen and a vaccine for a live immune system. Using this invention, the antibody titers are not confounded by the pre-existing accumulative antibodies in the serum from the same volunteers. The new findings allow for quantitatively measuring the antigen specific antibody production of the PBMC culture in post-vaccination or disease infection of recent antigen exposed human or animal blood samples. This method is specifically useful for determination of recent immune response during vaccine trials in endemic areas where the population already has pre-existing serum titers. It could also be used as a diagnostic method for identify in recent infections. Since this invention controls the soluble antibodies, it is more accurate and precise that serum antibody measurement. For immunogenicity evaluation, the invention measures secreting antibodies form recent vaccine or antigen activated B cells only. It reduces the clinical trial testing sample size than trials using serum antibody assays, which have large amount of pre-existing antibodies.

We describe here a novel method for measuring in vitro antibody secretion from the tissue culture of human B lymphocytes in peripheral blood mononuclear cells (PBMC) after oral vaccination with a killed cholera vaccine. Enzyme-linked immunosorbent assay (ELISA) titers of the antibody secreted in the cell supernatant were determined. The validation results demonstrated that human PBMC remained viable and continued to secrete antibodies (total immunoglobulin A and G (IgA and IgG) for up to 4 days of incubation at 37° C. with 5% $CO_2$ in cell cultures. The secreted antibody concentration correlated positively with the PBMC concentration and incubation time in the tissue culture and correlated negatively with the storage time of the whole blood at room temperature. In vitro assay of secreting antibody in the lymphocyte supernatant (i.e., the ALS assay) is capable of the detecting specific antibody response after oral vaccination with a killed whole-cell-plus-B-subunit cholera vaccine (WC-B) in healthy adults in a phase I clinical trial. Postimmunization PBMC secreted antibodies to cholera toxin in the cell supernatants. Antibody production did not require any in vitro antigen stimulation. In the ALS assay, antigen-specific antibody titers of prevaccination samples were barely detectable, whereas serum antitoxin ELISA titers in background of pre-vaccine samples were significantly higher than the ALS titers.

We conclude that, without any in vitro antigen stimulation after vaccination, PBMC secrete antibodies into the supernatants in the ALS assay. This assay can quantitatively measure the antigen-specific antibody production from the PBMC culture in post-vaccination blood samples.

4. Background

Postvaccination immunity is generally assessed via the use of antibodies in serum, but it is impossible to distinguish between recently produced antibodies and preexisting antibodies. Antibody levels in serum do not represent the latest immune responses accurately, because serum antibodies include the accumulated soluble antibodies that were induced by previous exposure to antigens.

Recent antigen exposure of mucosal T and B cells induces proliferation and differentiation of these cells (14, 25). The activated T and B cells circulate through the thoracic duct into the blood and eventually return to common mucosal sites, such as the lamina propria of the intestine, as matured plasma cells (2, 17, 20, 22, 23, 26).

To develop a sensitive surrogate for assaying local immunity, the lymphocytes traveling from local mucosal areas to the systemic blood circulation are used by methods for in vitro laboratory evaluations such as ELISPOT (6-10, 12, 15, 21; P. W. Lowry, L. M. McFarland, and H. K. Threefoot, Letter, J. Infect. Dis. 154:730, 1986). In its final step, ELISPOT measures the results of specific antibody-secreting cells (ASC) on a spot-forming gel (11-13, 15, 18; Lowry et al., letter). ELISPOT measures the number of antibody producing cells per $10^6$ PBMC following oral vaccination (11, 16). The quantification of antibodies secreted by a fixed concentration of PBMC is as important as the enumeration of ASC.

This invention is a novel method for measuring in vitro secreting antibody from human lymphocyte's supernatant, i.e., the ALS assay, which directly measures antibody secretions from PBMC of peripheral blood on a micro titer plate.

The ALS assay has been validated by the measurement of total immunoglobulin A (IgA) and IgG production under a series of tissue culture conditions (PBMC inoculation concentration, incubation time, and blood storage time). Then, $10^7$ PBMC was used to determine the antigen-specific antibodies to cholera toxin after the oral vaccination of a licensed *Vibrio cholerae* vaccine in a phase I clinical trial.

Two formulations of a killed whole-cell-plus-B-subunit cholera vaccine (WC-B) were used to immunize 12 healthy adults. A standard liquid formulation of the vaccine was stored continuously at 4° C., and a spray-dried formulation of the vaccine was placed at room temperature for 30 days. Volunteers were randomized to receive two doses of either vaccine in a double-blind manner. The vaccine induced an elevation in cholera toxin-specific antibodies in sera and induced secretive toxin-specific antibodies in the ALS assay.

The ALS assay is potentially an accurate surrogate for measuring recent antibody response and for the diagnosis of recent infections in humans.

DETAILED DESCRIPTION

I. Human Exposure to Antigen Via Vaccine Clinical Trial:

ALS Assay for *V. cholerae* antitoxin IgA and IgG during an oral cholera vaccine clinical trial: To apply the ALS assay for measurement of the antigen-induced specific humoral response, PBMC samples were collected during a safety and immunogenicity trial of an oral killed cholera vaccine in healthy adult volunteers. A standard liquid formulation of the vaccine and a spray dry formulation of the vaccine were compared. The liquid formulation was stored continuously at 4° C., but the dry vaccine was placed at room temperature for 30 days. Volunteers were randomized to receive two doses of either vaccine in a double-blind manner. Healthy volunteers between 18 and 50 years of age were recruited from the Baltimore area. Each volunteer received two doses of vaccine. Serum and PBMC were collected at days 0, 14, 21, and 24 after administration of dose one. The ALS assay was used to measure antitoxin IgA and IgG. (The complete evaluation of the vaccine trial will be reported elsewhere.)

The oral killed cholera vaccine was obtained from SBL Vaccine AB and consisted of $1.25 \times 10^{11}$ *V. cholerae* organisms. The heat-inactivated bacteria included Inaba-classical (Cairo 48; $2.5 \times 10^{10}$) and Ogawa-classical (Cairo 50; $2.5 \times 10^{10}$). The formalin-inactivated bacteria included Inaba El Tor (Phil 6973; $5 \times 10^{10}$) and Ogawa-classical (Cairo 50; $2.5 \times 10^{10}$) plus 1.0 mg of the recombinant B subunit of cholera toxin (3).

The dry vaccine was prepared from the same lot of vaccine as the liquid vaccine. To prepare the dry formulation, the same vaccine was mixed with syrup of the Cera-Vacx buffer and spray dried. One dose contained 10 g of dry powder, which was dissolved in 200 ml of water at the time of immunization (3).

To administer the liquid formulation, 3 ml of liquid vaccine (one dose) was mixed with 150 ml of Samarin buffer in a cup and was ingested orally, according to the instructions on the packet. To administer the dry vaccine, one dose (10 g of dry powder) was mixed with 200 ml of water and ingested orally. Eating and drinking was not allowed for 1 h before and after vaccination (3).

The volunteers were randomly assigned to receive two doses of either the dry vaccine or the liquid vaccine. Six volunteers were in each group. Peripheral blood was collected by using a Vacutainer on days 0, 14, 21, and 24. Samples (20 ml) of blood were obtained by using a Vacutainer into sodium citrate tubes (Blue Top; Becton Dickinson), and 10 ml without coagulant was placed in a Red Top tube and stored at 25° C.

II. Sample Processing:

Isolation of human PBMC: To perform the ALS assay, PBMC were isolated from blood samples via Histopaque layering. Thirty ml of human blood samples which were stored at room temperature for the same period of time from pre vaccination and post vaccination of the same volunteers were collected and stored at 25° C. for up to 3 days while remaining in the original vacutainer tubes containing anticoagulant (blue tubes). The total number of viable cells was counted using a microscope, a hemocytometer, and trypan blue staining.

A portion (30 ml) of blood was collected in citrate anticoagulant and diluted with sterile phosphate-buffered saline (PBS; Sigma) at up to 40 ml in a 50-ml sterile conical tube. The diluted blood was split into two tubes and layered onto 10 ml of Histopaque-1077 (Sigma H-8889) in a sterile 50-ml conical tube without mixing. These tubes were centrifuged at 1,200 (290×g) for 30 min. The mononuclear cell layer was transferred to a new tube and washed with 1×PBS. The cells were centrifuged at 1,200 rpm for 5 min in 40 ml of PBS. The cell pellet was resuspended in 10 ml of PBS. To determine the PBMC concentration, PBMC were stained with trypan blue and counted with a hemocytometer and trypan blue staining. The cells were pelleted by centrifugation (1,200 rpm [290×g], 5 min) and adjusted to a concentration of $10^7$ cells per ml with complete RPMI 1640 medium.

Making complete RPMI 1640 medium: A total of 50 ml of 10% fetal calf serum (FCS; C-Six Diagnostics, Inc.), 10 ml of 2% L-glutamine (Quality Biologicals, Inc. [catalog no. 118-084-060]), and 5 ml of antibiotics (amphotericin B-penicillin-streptomycin, 1% [Mixed]; Quality Biologicals, Inc. [catalog no. 120-096-050]) was added to every 500 ml of RPMI medium using a sterile technique. The medium was filtered via a 0.22-μm-pore-size filter if a precipitate appeared. The complete medium was stored at 4° C. for up to 30 days. To do the T-cell proliferation assay, the same RPMI 1640 complete medium was used except that FCS was replaced with 25 ml of human serum (5%; C-Six Diagnostics, Inc.).

Cell Culture of the PBMC for the ALS method: The condition of the in vitro culture of PBMC was defined by (i) PBMC concentration and volume during initial inoculation, (ii) incubation time, (iii) temperature, and (iv) air quality. A portion (1 ml) of the desired concentration of PBMC ($10^7$ PBMCs/ml determined via hemocytometer) in complete RPMI 1640 medium was inoculated under sterile conditions into the wells of a 24-well tissue culture plate. The cells were then incubated at 37° C. in 5% $CO_2$ for up to 96 hours. At the end of the incubation period, the tissue culture fluid was removed and stored at 20° C.

III. Immunoassay Quantification for Secreting Antibodies:

ELISA for measuring IgA and IgG antibodies of anti-*V. cholerae* Toxin (CTB subunit) and LPS (*V. cholerae* LPS): Antitoxin and anti-lipopolysaccharide (LPS)-specific IgA and IgG titers were measured by the enzyme-linked immunosorbent assay (ELISA) method using Gm1 and LPS as capture antigens. Microtiter 96-well, low-binding plates were first coated with a 100 μl of either 50 μg of Gm1 (Sigma) or 50 μg of *V. cholerae* LPS (Inaba 569B; Sigma) per ml in PBS overnight. The plates were then washed twice with 1×PBS and blocked with 100 μl of 0.1% bovine serum albumin (BSA)-PBS for 30 min at 37° C. The plates were washed three times with PBS-0.05% Tween 20. For the antitoxin assay, the Gm1 plates were supplemented with 100 μl of a 0.5-μg/ml concentration of cholera toxin B (CTB).

Test samples from the serum of volunteers (collected separately) or ALS supernatants were serially diluted in the plates using 0.1% BSA-PBS-Tween solution as a diluent. After 30 min of incubation, the plates were washed twice with PBS-Tween. Then, 100 μl of anti-human IgG or anti-human IgA conjugated with horseradish peroxidase (Jackson Laboratories) diluted in 0.1% BSA-PBS-Tween was added to each well. After the mixtures were washed, 100 μl of o-phenylenediamine (OPD; 1 mg/ml; Sigma) in 0.1 M sodium citrate buffer (pH 4.5) with 30% $H_2O_2$ (4 μl/10 ml) was added to each well. After 20 min, the plates were read at 450 nm in an automated ELISA reader.

Titers were calculated using a computer program to interpolate the dilution of serum that yielded an optical density of 0.4 above baseline. Pre-vaccine and post-vaccine sera were tested simultaneously in the same plate.

ELISA for total human IgA and IgG: Total IgA and IgG levels were measured by using conjugate antibodies of goat anti-human IgA and IgG in ELISA. DynTech Immunolon I plates were coated with 100 µl of 2-µg/ml concentration of goat anti-human IgA α-chain-specific (Jackson Laboratories) or goat anti-human IgG Fc-specific (Jackson Laboratories). The plates were incubated overnight at 4° C. Each plate was washed with 1×PBS and blocked with 100 µl of 1% BSA-1×PBS at 37° C. for 30 min. The plate was then washed with PBS again. A 100-µl portion of ALS supernatant sample with the desired dilutions was then added to the plate. Standard human IgA and IgG with twofold dilutions were added to each plate as a standard.

For total IgA measurement, the plates were incubated for 60 min at 37° C. and washed with PBS-0.05% Tween 20. The plate was then conjugated with goat anti-human IgA (peroxidase conjugated, α-chain specific; Jackson Laboratories). For total IgG measurement, the plates were conjugated with goat anti-human IgG heavy and light chain, (peroxidase conjugated; Jackson Laboratories). The plates were incubated at 37° C. for 60 min and washed with PBS-0.05% Tween 20. Then, 100 µl of OPD substrate (Sigma) was added. Finally, the plates were read in an ELISA reader at 450 nm.

Measurement of total IgA and IgG secretion abilities for ALS samples processed at days 0, 1, 2, and 3 at room temperature: Titration of the effect of blood storage on the ability of PBMC to secret the antibodies was done with blood samples from two healthy adults. The blood was stored at day 0, day 1, day 2, and day 3 at room temperature. These same aliquots of blood were processed for PBMC isolation and adjusted to $10^7$ cells per ml in complete RPMI 1640 medium. Then, 1 ml of each sample in the 24-well tissue culture plate was inoculated and incubated at 37° C. with 5% $CO_2$ for 48 h. Cell supernatants were collected for the measurement of total IgA and IgG by ELISA.

Titration of total antibody secretion versus PBMC concentration in the ALS assay: The effect of different concentrations of PBMC on antibody production in the ALS assay was measured in freshly isolated PBMC after 96 h of incubation. Blood samples from two healthy adults were processed for PBMC isolation and adjusted to $10^7$, $10^6$, and $10^5$ cells/ml. Next, 1 ml of each concentration was inoculated into a 24-well cluster tissue culture and incubated at 37° C. with 5% $CO_2$. Supernatants were collected and stored at −20° C. Antibody titers were determined via ELISA for total IgA and IgG.

Titration of total antibody aecretion versus PBMC incubation time in the ALS assay: The effect of different incubation times of PBMC cultures on antibody production in the ALS assay was measured in freshly isolated PBMC at $10^7$ cells/ml. Blood samples from two healthy adults were processed for PBMC isolation and adjusted to $10^7$ cells/ml. Then, 1 ml of these cells was incubated for either 1, 2, 3, or 4 days at 37° C. with 5% $CO_2$. The supernatants were collected, and ELISA for total IgA and IgG was performed.

Results:

Human blood sample storage and viability counts as determined with a hemocytometer under a ×36 lens at room temperature: To check PBMC yield with the effect of blood sample storage from the same subjects, a 10-ml portion of blood yielded about 150×$10^6$ PBMC after storage at room temperature up to 48 h. By day 3, the PBMC yield dropped by about 30% on average (Table 1).

TABLE 1

Stability of Human PBMC at 25 C. up to 72 hours (Total Cell counts under microscope & T cell proliferation (Ratio ConA:Non-ConA))

| | 0 hrs | 24 hrs | 48 hrs | 72 hrs |
|---|---|---|---|---|
| Average Total PBMC yield[a] (+/− SD) × $10^6$/10 ml blood | 151 (+/−26) | 132 (+/−46) | 142 (+/−27) | 103 (+/−57) |
| t test P Value[a] | | 0.29 | 0.35 | 0.13 |
| Average T cell proliferation[b] (+/− SD) | 33.9 (+/−12.7) | 37.6 (+/−19.2) | 6.9 (+/−10.2) | 9.8 (+/−12.8) |

[a]Three human normal blood samples were obtained with citrate anticoagulant and stored at 25° C.. Each day, 10 ml of each sample was processed for PBMC isolation up to 72 h via hemocytometer under a ×36 microscope lens. Average PBMC yields and standard deviations of the three volunteers are reported in the table. A one-tailed t test was performed (P) between day 0 and any of the other days for the total viable cell counts.
[b]T cell proliferation is also measured as a quality character measure for these PBMC cells. Three blood samples from healthy volunteers were collected (no vaccination) and stored at 25° C.. These samples were processed at day 0, day 1, day 2, and day 3, and the cell concentrations were adjusted to $10^6$ cells/ml. On a 96-well tissue culture plate, 100 µl of each PBMC sample was added to each well. To stimulate PBMC, 100 µl of a 2-ng/ml concentration of ConA per ml was added to each well. The cells were harvested and counted for $H^3$ incorporation. The results are expressed as the ratio of sample counts with ConA to corresponding control counts without ConA.

Negative control: antibody level in PBMC. There was no detectable antigen-specific or nonspecific IgA or IgG titer in $10^7$ sonicated PBMC cell pellet from the *V. cholerae*-vaccinated-volunteer blood samples.

Effect of blood storage on total IgA secretion at room temperature. The results indicated that blood storage over time was a negative factor for IgA production in the ALS assay. After 24 h of storage, the same sample's total IgA yield dropped from 450 to 50 µg/ml in the in vitro cultures. However, samples stored for 1, 2, and 3 days produced similar and significant amounts of total IgA (50 µg/ml) in the supernatants.

The average total IgA level of two normal human blood samples, which were stored at 25° C. before PBMC processing, was determined. The supernatants were taken after 96 h of incubation, and the initial concentrations were 7 logs of the cells. The total IgA levels on storage days 0, 1, 2, and 3 were 459 (range, 417 to 500), 62 (range, 62 to 62), 49 (range, 38 to 60), and 51 (range, 44 to 59), µg/ml, respectively.

Total IgA Secretion Increases with the Increase of PMBC Concentrations in the ALS Assay:

When cells were incubated for 96 h in tissue culture, the total IgA production increased exponentially with the increase in the concentration of PBMC cultured initially. At from $10^5$ to $10^7$ cells, the log of the IgA concentration was linearly related to the log of the initial cell concentration. The slope appeared to increase with higher cell concentrations (Table 2).

TABLE 2

PBMC cell Concentration (log concentration) Vs. Total IgA (log Total IgA concentration)

| log con | Log IgA (ug/ml) day 4 Inc. | Log IgA (ug/ml) day 3 Inc. | Log IgA (ug/ml) day 2 Inc. |
|---|---|---|---|
| 7 | 2.66 (2.62–2.70) | 2.30 (2.08–2.44) | 2.06 (1.87–2.20) |
| 6 | 1.66 (1.47–1.79) | 1.09 (1.05–1.13) | 0.82 (0.58–0.97) |
| 5 | 1.29 (1.04–1.45) | 0.80 (0.61–0.93) | 0.26 (0.00–0.45) |

[a] Average data of two normal human PBMC samples adjusted with 1 ml of the initial concentration at log 7, 6, and 5 of cells per milliliter. Supernatants were collected after either 2, 3, 4 days of incubation. Total IgA was measured and is expressed in log IgA (micrograms/milliliter, with range from lowest to highest).

Total IgA secretion increases with the increase of PBMC incubation time in the ALS Assay: Total IgA secretion increased linearly with time of incubation (2 to 4 days) when $10^7$ PBMC of day 0 blood were used in the ALS assay. The slope appeared to increase with longer incubation days. The total IgA from the samples of two normal human volunteers was measured in the supernatants of an ALS assay following incubation for 2, 3, and 4 days, and the results, obtained with a 1-ml portion of PBMC ($10^7$ cells per ml), were averaged together. The IgA levels (ug/ml) were determined to be 116 (range, 74 to 157), 197 (range, 120 to 274), and 459 (417 to 500) μg/ml for incubation days 2, 3, and 4, respectively.

Linear regression model. There was a significant linear relationship between the log IgA and log cell concentrations and the incubation time. The log IgA in (micrograms per milliliter) is the dependent variable. The independent variables are the incubation time and the log cell concentration (based on day 0 storage data). The regression equation is as follows: log IgA (μg/ml)=−4.632+0.424 incubation day+ 0.794 log con. According to this model, if the incubation time increases by 1 day, 0.424 log of total IgA will be secreted. If the cell concentration is increased by 1 log, 0.794 log of total IgA would be secreted. The linear regression model was highly significant, with an F score of 61.9, a P value of 0.000, and a regression coefficient of 0.89 (Table 3).

ALS IgA anti-CTB for cholera vaccine volunteers: Immunization with either formulation of the oral killed cholera vaccine in humans induced specific IgA anti-CTB 14 days after the first dose and 7 days after the second dose in the ALS assay. The peak of the IgA ALS titer was at day 21 and started to decrease by day 24 (Table 3). The liquid formulation of the oral vaccine induced significantly higher IgA to CTB than the dry formulation in the ALS assay (Table 3).

However, the titers in serum showed a very different result from those of the ALS assay. The titers in serum showed higher titers with the dry formulation. An antibody titer continuously increased until day 24 (Table 3).

ALS IgG anti-CTB: In comparison to the IgA response, the ALS IgG anti-CTB response of the liquid formulation was significantly higher than that of the dry formulation. Both formulations induced significant ALS antibody response 14 days after the first dose and 7 days after the second dose. The peak of ALS IgG anti-CTB response was at day 21 and dropped at day 24 (Table 4). Similar to the IgA response, the dry vaccine induced IgG titers in serum that were higher than those with the liquid vaccine. The titers in serum continuously increased until day 24 (Table 3)

TABLE 3

Antibody responses in Serum, and ALS assays from the 12 volunteers who were orally vaccinated with either the dry or the liquid formulation

| | Dry Formulation GM (+/− SD) (Folds to Day 0) | Liquid Formulation GM (+/− SD) (Folds to Day 0) |
|---|---|---|
| Serum IgA antitoxin[a] | | |
| Day 0 | 35 (6–219) (1) | 32 (13–78) (1) |
| Day 14 | 89 (23–347) (2.5) | 46 (17–120) (1.4) |
| Day 21 | 269 (148–490) (7.7) | 123 (60–251) (3.8) |
| Day 24 | 251 (132–479) (7.2) | 174 (78–427) (5.4) |
| Serum IgG antitoxin[a] | | |
| Day 0 | 120 (58–251) (1) | 93 (54–162) (1) |
| Day 14 | 191 (78–468) (1.6) | 148 (60–363) (1.6) |
| Day 21 | 389 (123–1230) (3.2) | 339 (155–741) (3.6) |
| Day 24 | 575 (263–1230) (4.8) | 372 (78–776) (4) |
| ALS IgA antitoxin[b] | | |
| Day 0 | 1 (0.2–1.12) (1) | 0.86 (0.28–2.57) (1) |
| Day 14 | 0.91 (0.43–2.34) (0.9) | 1.27 (0.43–3.80) (1.5) |
| Day 21 | 1.92 (0.66–5.75) (1.9) | 4.38 (0.91–20.89) (5.1) |
| Day 24 | 0.66 (0.55–1.02) (0.7) | 2.64 (0.55–12.88) (3.1) |
| ALS IgG antitoxin[b] | | |
| Day 0 | 0.28 (0.07–1.05) (1) | 0.66 (0.13–3.31) (1) |
| Day 14 | 0.47 (0.09–2.4) (1.7) | 1.44 (0.49–4.27) (2.2) |
| Day 21 | 1.30 (0.63–2.69) (4.6) | 4.22 (1.07–16.6) (6.4) |
| Day 24 | 0.68 (0.32–1.48) (2.4) | 3.50 (0.71–17.38) (5.3) |

[a]Anti-CTB IgG and IgA levels from volunteer sera were measured via ELISA of GM1-CTB-coated plates. Titers were determined by use of a hyperbolic curve. Then the geometric mean titer (GMT) of same-day determinations for each group of volunteers were calculated by using Excel software. The fold increase values are also reported. Anti-CTB ALS IgG and IgA levels from volunteer PBMC samples were measured via ELISA of GM1-CTB-coated plates. Titers were determined by use of a hyperbolic curve. Then, the GMT values of same-day determinations for each group of volunteers were calculated by use of Excel software. The fold increase values are also reported.

Discussion:

ALS, a specific, reliable, and accurate immunoassay, was developed for the evaluation of fresh antibody production from circulating mucosal secreting B lymphocytes. In the human trial described here, the ALS assay detected the significant antitoxin increases induced by either formulation of the oral vaccine. The ALS results indicated a peak booster antitoxin response at day 21, which is 7 days after the second dose, that started to decrease at day 24. (Complete results for this clinical trial will be reported separately.)

By assaying only antibodies secreted by circulating cells, the ALS method controlled the confounding effect of accumulative antibody in the serum samples, which contain both recent and preexistent soluble antibodies. Since the serum portion of the blood sample has been removed in the ALS assay, this assay measures only the secreting antibodies. When the ALS assay was performed, antibody titers from prevaccination samples were barely detectable, but background titers in serum were found in prevaccination samples.

In the ALS assay, vaccine-activated mucosal lymphocytes were cultured in vitro for 2 to 4 days. The secreted antigen-specific immunoglobulins in the supernatants of tissue culture were qualitatively and quantitatively measured. These PBMC are believed to be the circulating mucosal lymphocytes. ALS measures the change in host antibody response with the amount of nonstimulated, in vitro antibody produced at different postvaccination time points. This test allowed us to monitor the magnitude of the mucosal B-cell's antibody production strength during the course of immunization.

Antibody production of lymphocytes requires multiple signals and optimal cognitive interactions, such as receptor engagement between antigen-presenting cells (APC), T cells, and B cells. The isolated PBMC layer from blood samples contains a mixture of these components. In the ALS system, antibody production is enhanced by cell concentration and incubation time synergistically. High concentrations of cells in a contained space enhances the cognitive distance of cell-to-cell interaction. As the efficiency of cell interaction increased, antibody secretion increased exponentially. When the blood samples were subjected to a long storage condition such as at room temperature for 2 days, it is possible that some key components, such as the cytokines necessary for antibody secretion, start to deteriorate.

Since 1963, immunoglobulin secretion at the cellular level has been assayed by hemolytic plaque assay (1). Hemolytic assay can detect cells secreting complement-binding antibodies against erythrocytes (4, 5, 24). This assay has limitations when it is applied to soluble antigens passively adsorbed to red blood cells (24). Inconsistent results had generally been associated with difficulty in coupling antigen efficiently to red cells (4, 5, 24). Additionally, the hemolytic assay did not permit quantification of secreted molecules. ELISPOT is a qualitative assay for ASC. It requires a subjective reading of the formed spots.

The ALS assay quantifies the amount of antibody secreted and the strength of the antibody production for a fixed number of PBMC. Logistically, ALS assay does not require live bacteria during testing as the vibriocidal tests. Compared to the ASC assay, the ALS assay uses antibody supernatants of the PBMC as its final specimens rather than the PBMC. In terms of the storage of samples, cells may be stored at −70° C. for up to 6 months for the ASC assay, whereas ALS supernatants can be stored at 4° C. or −20° C. for a much longer time. The ALS assay final result is based on readings from the ELISA reader rather than the subjective determinations of spot formation on gels in the ASC assay and turbidity in the vibriocidal assay. The major limitation of the ALS assay is the requirement of the use of fresh blood to yield a high quantity and quality of PBMC.

This assay is specifically useful for the determination of a recent immune response during vaccine trials in areas where the disease is endemic and where the population already has preexisting serum titers. It could also be used as a diagnostic method for identifying recent infections.

Publications:

A manuscript containing information about this technology entitled "Development of a Novel In Vitro Assay (ALS Assay) for Evaluation of Vaccine-Induced Antibody Secretion from Circulating Mucosal Lymphocytes" will be published in the May, 2001 issue of *Clinical and Diagnostic Laboratory Immunology*. Page 482-488, Manuscript attached.

Commercial Use of This Patent:

This technology can be developed into a commercial testing kit. It will contain blood collection tubes to collect human or animal bloods with anticoagulant. Then provide the histopaque reagent for layering the PBMC. Use a 12 well tissue culture flask to perform the PBMC tissue culture with provided and concentrated MEM media. Provide ELISA plates coated with specific antigen, washing, blocking and diluting buffers, and species specific conjugates and substrate to allow customers to measure the antigen specific secreted antibody levels.

This technology is a novel method for measuring in vitro antibody secretion from tissue culture of B lymphocytes in the peripheral blood mononucleus cells (PBMC). Instead of enumerating antibody-secreting cells in the ELISPOT assay, this technology quantifies recent antigen specific secreted antibodies from a fixed concentration of PBMC cells rather than accumulative soluble antibodies in the serum. A clinical trial using this technology demonstrated that the post-immunization human PBMC cells secreted antibodies to cholera toxin in the cell supernatants without any in vitro antigen stimulation after an oral vaccination with a killed cholera vaccine. Using this invention, the antibody titers are not confounded by the pre-existing accumulative antibodies in the serum from the same volunteers. The new findings allow for quantitatively measuring the antigen specific antibody production of the PBMC culture in post-vaccination of recent antigen exposed human or animal blood samples. This assay is specifically useful for determination of recent immune response during vaccine trials in endemic areas where the population already has pre-existing serum titers. It could also be used as a diagnostic method for identify in recent infections. Since this invention controls the soluble antibodies, it is more accurate and precise that serum antibody measurement. For immunogenicity evaporation, the invention measures secreting antibodies form recent vaccine activated B cells only. It reduces the clinical trial testing sample size than trials using serum antibody assays, which have large amount of pre-existing antibodies.

The invention claimed is:

1. A method for detecting the level or the presence of antigen-specific antibodies secreted from a subject's antibody secreting cells, said method comprising the steps of (i) obtaining a sample comprising the supernatant of an in vitro culture of antibody secreting cells isolated from a subject after excluding serum antibodies from the in vitro culture, and (ii) determining the level or the presence of said antigen-specific antibodies in said sample;

wherein the antibody secreting cells are in vivo stimulated by an antigen in the subject before isolating the antibody secreting cells from the subject, and the antibody secreting cells or the culture are not in vitro stimulated by the antigen or a part thereof prior to the determining step.

2. The method of claim 1, wherein said antibody secreting cells are peripheral blood mononuclear cells.

3. The method of claim 1, where in said antibodies comprises whole immunoglobulins or fragments thereof.

4. The method of claim 1, wherein said subject is a human.

5. The method of claim 1, wherein said antigen is derived from a pathogen.

6. The method of claim 1, wherein said antigen is an antigenic part of a vaccine.

7. The method of claim 1, wherein said antigen is derived from an antigenic substance, which is capable of eliciting an antibody immune response specific to said antigen in the said subject.

8. The method of claim 1, wherein said subject is immunized with a vaccine comprising said antigen before the obtaining step.

9. The method of claim 1, wherein said subject is infected with a pathogen from which said antigen is derived before the obtaining step.

10. The method of claim 1, wherein said subject is in vivo stimulated with said antigenic substance before the obtaining step.

11. The method of claim 1, wherein the level or the presence of said antigen-specific antibodies is determined by an enzyme-linked immunosorbent assay.

12. The method of claim 1, wherein the level or the presence of said antigen-specific antibodies is determined by an assay that quantifies or determines the presence of said antigen-specific antibodies.

13. The method of claim 1, wherein the level or the presence of said antigen-specific antibodies is determined by an immunoassay.

14. The method of claim 1, wherein the subject is in vivo stimulated with a vaccine comprising the antigen.

* * * * *